United States Patent [19]

Buchanan et al.

[11] Patent Number: 4,721,858
[45] Date of Patent: Jan. 26, 1988

[54] VARIABLE PRESSURE IONIZATION DETECTOR FOR GAS CHROMATOGRAPHY

[75] Inventors: Michelle V. Buchanan, Knoxville; Marcus B. Wise, Oak Ridge, both of Tenn.

[73] Assignee: The United States of America as represented by the United States Department of Energy, Washington, D.C.

[21] Appl. No.: 854,236

[22] Filed: Apr. 21, 1986

[51] Int. Cl.⁴ ............................................ G01N 27/70
[52] U.S. Cl. .................................... 250/379; 250/382
[58] Field of Search ............... 250/381, 379, 384, 383, 250/382; 324/469, 465, 464; 436/36, 149, 178; 422/54

[56] References Cited

U.S. PATENT DOCUMENTS

| | | | |
|---|---|---|---|
| 3,601,609 | 8/1971 | Yauger, Jr. | 250/375 |
| 4,137,453 | 1/1979 | Siegel | 250/382 |
| 4,166,379 | 9/1979 | Bradshaw | 73/23.1 |

OTHER PUBLICATIONS

Michelle V. Buchanan and Geraldine Olerich, "Differentiation of Polycyclic Aromatic Hydrocarbons Using Electron Capture Negative Chemical Ionization", *Organic Mass Spectrometry*, vol. 19, No. 10, (1984), pp. 486–489.

Littlewood, A. B., "Electron Capture Detector" *In: Gas Chromatography: Principles, Techniques, and Applications* (New York, Academic Press, 1970), pp. 315–322.

*Primary Examiner*—Janice A. Howell
*Assistant Examiner*—Constantine Hannaher
*Attorney, Agent, or Firm*—Stephen D. Hamel; Judson R. Hightower

[57] ABSTRACT

Method and apparatus for differentiating organic compounds based on their electron affinity. An electron capture detector cell (ECD) is operated at pressures ranging from atmospheric to less than 1 torr. Through variation of the pressure within the ECD cell, the organic compounds are induced to either capture or emit electrons. Differentiation of isomeric compounds can be obtained when, at a given pressure, one isomer is in the emission mode and the other is in the capture mode. Output of the ECD is recorded by chromatogram. The invention also includes a method for obtaining the zero-crossing pressure of a compound, defined as the pressure at which the competing emission and capture reactions are balanced and which may be correlated to the electron affinity of a compound.

6 Claims, 13 Drawing Figures

VARIABLE PRESSURE IONIZATION DETECTOR FOR GAS CHROMATOGRAPHY

BACKGROUND OF THE INVENTION

The present invention relates to a method and apparatus for ionization detection useful in gas chromatography (GC). More specifically, the invention provides for a variable pressure ionization detector, in particular an electron capture detector in a variable pressure vacuum chamber, which allows selectivity in the detection of gaseous organic compounds by variation of the pressure and/or chemical composition of the ionization reagent gas in the detector.

Radiation ionization cells have heretofore been used extensively for gas chromatographic detection. The basic design typically consists of a two electrode, low volume cell which houses a small quantity of a beta particle emitter such as $^3H$ or $^{63}Ni$. Interaction of the beta radiation with the reagent gas, GC carrier gas, and effluent generates a population of free electric field across the electrodes. Depending on the nature of the carrier and/or reagent gas used, as well as the geometry of the cell, the measured electron current will either increase (due to electron emission) or decrease (due to electron capture) as compounds elute from the GC column and enter the detector cell. This response is amplified and recorded to generate a chromatogram.

Numerous variations of this basic cell design have been disclosed, some of which have selective response and others of which are essentially universal detectors. The more important of these include the electron capture detector (ECD), the argon ionization detector, the micro argon detector, the helium ionization detector, and the cross-section ionization detector. With the exception of the ECD, these detectors respond by means of various reaction mechanisms which cause electron emission (increased current) as eluted compounds traverse the cell. Response is also affected by the manner in which free electrons are collected. For example, the electric field applied to the cell may be either continuous (DC) or pulsed. Wider dynamic range, greater stability, and fewer aberrations are typical characteristics of the pulsed systems.

In cross-section ionization detectors, compounds are directly ionized by collision with beta particles and high energy electrons. The measured current of ejected electrons is a function of compound concentration and ionization cross-section.

Both the argon and helium ionization detectors generate a response through ionizing collisions of metastable noble gas atoms with the GC effluent. By using high purity argon or helium as the carrier gas and/or by adding these gases to the cell as reagents, a high concentration of metastable atoms is produced by the beta radiation. Since the metastable states of these atoms are above the ionization potentials of most compounds, ionizing collisions occur as eluted compounds enter the detector. Again, the increase in free electrons is measured and recorded as a response. This is a more efficient process than cross-section ionization, and therefore the sensitivity is higher.

Electron capture detectors in general have been used in gas chromatography as disclosed in "Gas Chromatography Principles, Techniques and Applications," Littlewood, A. B., *Electron Capture Detectors*, 2nd Ed., Academic Press, N.Y., (1970), pp. 315-322. The electron capture cell contains a small quantity of $^{63}Ni$ foil which emits beta particles. Under conventional operating conditions, i.e., atmospheric pressure, the beta particles collide with atoms and molecules in the GC carrier gas, usually argon with 10% methane, resulting in a large population of free electrons formed by collisions of methane with metastable argon atoms. Ejected electrons are rapidly thermalized through collisions with neutral methane and argon. Steady state currents (standing currents) of $10^{-8}$ to $10^{-9}$ amps are produced. As compounds elute from the GC column and enter the detector cell, they capture electrons (provided that they have a high enough electron affinity) and cause a decrease in the measured electrical current. This change in current is measured and recorded to produce a gas chromatogram.

Negative ion chemical ionization mass spectrometry has been shown to be a useful method for discriminating, for example, between isomeric polycyclic aromatic hydrocarbons (PAH). The article "Differentiation of Polycyclic Aromatic Hydrocarbons Using Electron Capture Negative Chemical Ionization", Buchanan, M. V. and Olerich, G., *Org. Mass. Spec.* Vol. 19, No. 10, 1984 describes the use of electron capture ionization of PAH compounds to produce molecular ions, $[M]-$. Differentiation of isomeric PAH compounds could be effected based on relative differences in electron affinity. These experiments also indicated that the degree of discrimination was pressure dependent and increased at lower pressures. Because of the similar nature of the processes that occur in a conventional electron capture detector (ECD) used for gas chromatography it was believed that similar isomeric discrimination could be achieved with a GC by operating an ECD at reduced pressures.

The known prior art arrangements have always been operated at atmospheric pressure, so that a fixed number of low energy electrons (for a given carrier gas) are available for electron capture. A threshold electron affinity is thus established, above which electrons are captured and below which electrons are not captured. This phenomenon can be used to advantage, for example, in differentiating two isomers, one of which has an electron affinity above the threshold and the other below. If both isomers are above the threshold, however, such differentiation is not possible, since both compounds will affect the measured electrical current. The prior art electron capture detectors are thus limited in their usefulness for differentiating compounds.

DISCLOSURE OF THE INVENTION

It is accordingly an object of the invention to provide a method and apparatus for ionization detection and differentiation of compounds by means of an electron capture detector which detects differences in compound electron affinity.

It is another object of the invention to provide a method and apparatus, as above, which can detect and differentiate compounds through variation of an electron affinity threshold.

It is yet another object of the invention to provide a method and apparatus, as above, which can operate either in an electron capture mode or an electron emission mode.

These objects are achieved by an apparatus for detection and differentiation of organic compounds by electron affinity which comprises an electron capture cell, means for injecting gaseous compounds into the cell, a pair of electrodes communicating with the cell for detection and measurement of electric current fluctuation in the cell, and means for varying the pressure in the cell, the electric current variation being a function of the composition of gaseous compounds in the cell.

The objects of the invention are also achieved by a process for detection and differentiation of organic compounds by electron affinity, comprising the steps of injecting a gaseous mixture containing at least two organic compounds into an electron capture cell, maintaining the pressure in the cell below atmospheric pressure, detecting the variation in electrical current in the cell due to one of absorption and emission of electrons by the organic compounds, and differentiating the compounds based on the electrical current variation.

BRIEF DESCRIPTION OF THE DRAWINGS

For a full understanding of the invention, the specification should be read in conjunction with the drawings, wherein.

DETAILED DESCRIPTION OF THE PREFERRED EMBODIMENTS

The method and apparatus of the invention approximates the conditions of a mass spectrometer chemical ionization source using an electron capture detector enclosed in a variable pressure chamber capable of producing a high vacuum. Detector selectivity (discrimination) can be achieved by varying the pressure and chemical composition of the reagent gas in the cell. This provides a versatile, low-cost means for enhancing the analytical capabilities of a conventional gas chromatograph.

Figure 1:
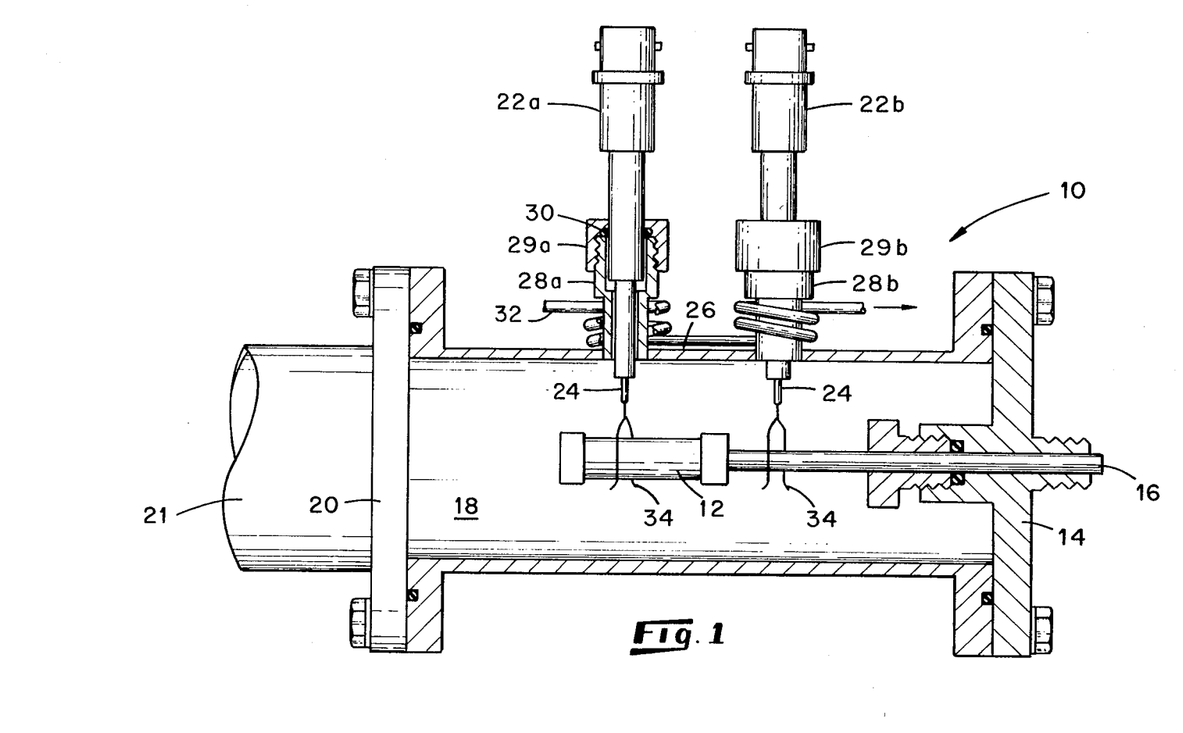
FIG. 1 is a partial cross-sectional view of a variable pressure detector cell and vacuum chamber in accordance with one embodiment of the present invention.

One embodiment of the variable pressure ionization detector of the invention is illustrated in FIG. 1 and is generally indicated by the number 10. An electron capture detector (ECD) cell 12 is mounted on a flange 14 which is preferably of stainless steel and which is capable of supporting a high vacuum. The flange 14 includes a sample inlet port 16 communicating with the cell 12 and into which gas samples, such as effluent from a GC column, are injected together with reagent gas. The electron capture cell is entirely enclosed within a vacuum chamber 18 in which the pressure can be varied from about atmospheric to very high vacuum, e.g. pressures of about 0.1 torr or less. Flange 14 provides sealing at one end of the chamber 18 while a flange 20 seals the other end from the atmosphere and is connected to a source of variable pressure such as a vacuum manifold 21 of conventional design.

Situated outside the chamber 18 are anode and cathode electrodes 22(a) and 22(b) of similar design each having an electrical feedthrough 24 which passes through the wall 26 of the chamber at a location adjacent to the detector cell 12. For this purpose, the wall 26 preferably has a pair of threaded couplings 28(a) and 28(b) which matingly engage respective couplings 29(a) and 29(b) on the electrodes. The electrodes are provided with O-rings 30 or equivalent sealing members which seat the electrodes into the couplings 28(a), 28(b) as shown in FIG. 1, and which seal the electrical feedthroughs against vacuum leakage from the chamber 18. With this arrangement, the electrical feedthroughs can be removed from the chamber 18 simply by loosening the couplings 29(a) and 29(b). Suitable such sealing arrangements can be made by slight modification of commercially available fittings, for example, CAJON ® Ultra-Torr Fittings.

A cooling coil 32 prevents overheating of the electrodes during operation and is wrapped around the couplings 28(a) and 28(b). Extending from the electrical feedthrough 24 of each electrode to the cell 12 is an electrode wire 34 which detects and measures the current passing through the cell.

Figure 2:
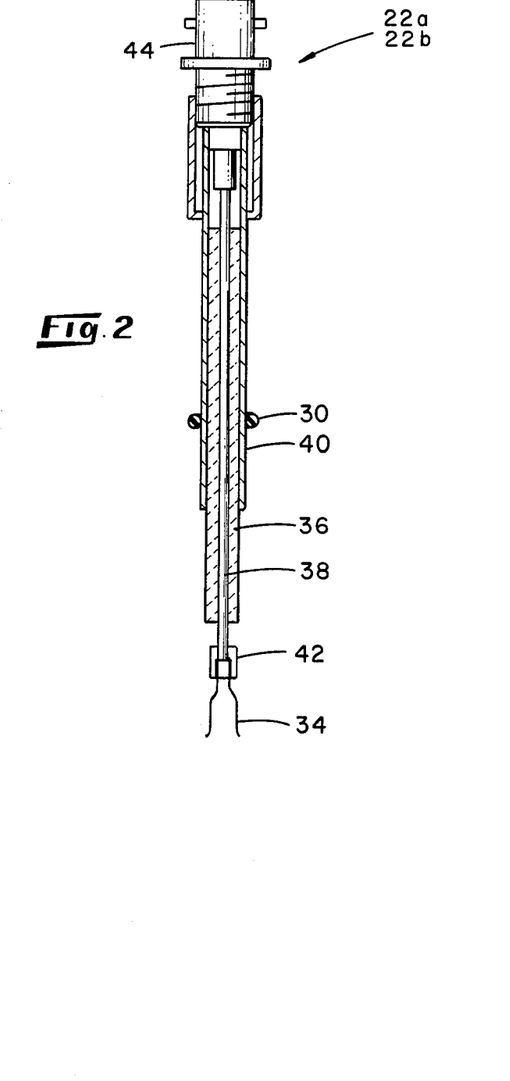
FIG. 2 is a cross-sectional view of a vacuum feedthrough electrode used in the invention.

A representative electrode is illustrated in greater detail in FIG. 2. A ceramic insulator 36 surrounds an electrical feed 38 constructed of, for example, No. 16 wire. The ceramic 36 is surrounded by a sheath 40 preferably of stainless steel tubing. An electrical crimp connector 42 provides electrical connection between the electrical feed 38 and the electrode wire 34. The electrode wire is preferably in the form of a spring clip which engages the ECD cell 12 along its perimeter. A BNC cable connector 44 connects the electrode to an electrical source (not shown).

The operation of the apparatus will now be described. As mentioned above, beta particles colliding with atoms and molecules in the carrier gas injected into the column and reagent gas injected into the cell produce low energy electrons. These electrons in turn are measured by the electrodes 22(a) and 22(b) as an electric current. At atmospheric pressure, electron affinity of the compounds must be at least about 0.5 eV for electron capture to occur, except when reactions occur such as with oxygen or water that may form a new species with an electron affinity of greater than 0.5 eV.

By changing the pressure of the carrier gas in the detector cell, the chemical reactions that occur can be controlled. Thus, some compounds that capture electrons under conventional, atmospheric pressure conditions will not do so under low pressure conditions, and are thereby selectively eliminated from the chromatogram. Further selectivity can be achieved by mixing small quantities of different reagent gases will the GC effluent prior to entering the detector cell as will be discussed in greater detail hereinafter. In the selective mode, it is possible to differentiate between isomeric compounds having electron affinity values with a difference of at least about 0.03 eV. At least one of the compounds should also be capable of capturing electrons. This enables a virtually limitless range of possible applications. Most organic compounds can be detected under low pressure conditions either by capture or emission of electrons.

At very low pressures, i.e. less than about 1 torr, cross-section ionization is favored, in which beta particles emitted in the cell directly ionize compounds as they elute from the GC column, forming positive ions and electrons. The electrons produced under these conditions generate an electrical current that is measured and recorded to produce a chromatogram. Since virtually any chemical can be ionized in this manner, a chromatogram display peaks for every compound in a sample. The detector thus behaves as a "universal" detector under these conditions. However, because of the low efficiency of this process, this mode of operation is the least sensitive. At the same time, the mode of operation may be useful for detecting compounds present in the concentration range of 0.1%–100% that may otherwise cause detector saturation.

At pressures of from about 1–10 torr, sufficient pressure exists for ionization of the carrier and reagent gas. For example, when argon is used as the carrier or reagent gas, the detector behaves as an argon ionization detector in which metastable argon atoms ionize the organic GC effluent to produce a measurable increase in electron current:

$$Ar^* + M \rightarrow Ar + M^+ + e^-$$

The detector therefore responds for any compound that has an ionization potential less than the energy of metastable argon. This includes virtually all organic compounds. At these low pressures, however, electron thermalization is not effective enough to allow significant electron capture. This mode of operation is considerably more sensitive than cross-section ionization.

Figure 10:
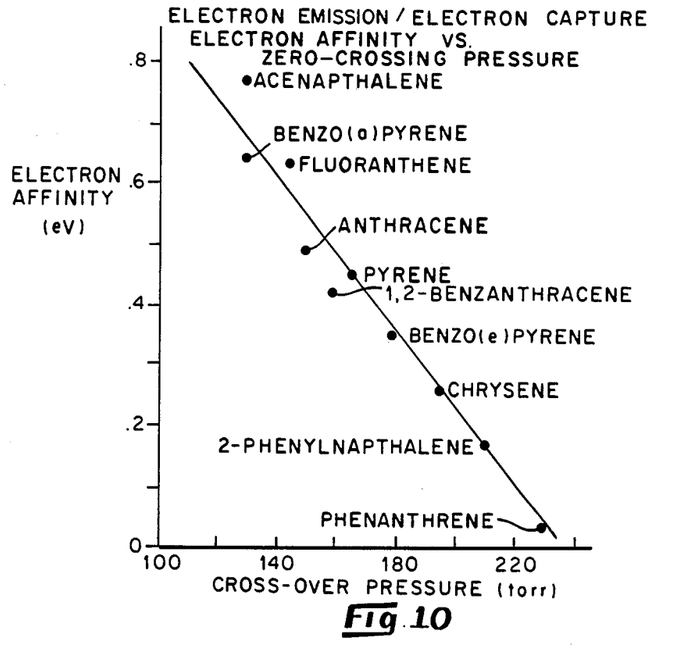
FIG. 10 is a graph of electron affinity versus zero-crossing pressures for the compounds of FIG. 8.

At pressures of from about 100 to about 250 torr, competition between electron emission (argon ionization) and electron capture controls the response of the detector. These competing reactions are strongly dependent on cell pressure and the electron affinity of the unknown compound. Thus, by changing the pressure only slightly, the response can be altered so that specific compounds can be analyzed in the presence of interfering components. The point at which equilibrium exists between electron capture and electron emission for a given compound is referred to as the zero-crossing point, and is determined by obtaining chromatograms at several discrete pressures and noting the pressure at which no detector response occurs. Experiments with polycyclic aromatic hydrocarbons (PAH) have shown that there is an excellent correlation between calculated electron affinity values and the pressure within the cell at which equilibrium exists between electron capture and electron emission. To measure relative electron affinities, the zero-crossing pressure of the unknown compound is plotted on a graph of electron affinity vs. zero-crossing pressure. The line is determined by two or more calibration compounds with known electron affinity. FIG. 10, for example, is a plot of electron affinity vs. zero-crossing pressure for 10 PAH.

The apparatus of the present invention can also be utilized as an "electron-affinity spectrometer" which enables the zero-crossing pressure to be determined in a single experiment, rather than in a series of experiments at discrete pressures. This method is characterized by maintaining a constant flow of the compound through the detector and then rapidly varying the detector pressure by pulsing the reagent gas into the system. By recording the electron current generated this way and by subtracting the background current due to the pure reagent, it is possible to easily measure the zero-crossing point.

As mentioned above, the type of reagent gas can have an effect on selectivity and consequently on the zero-crossing pressure. Several reactions are believed to take place and compete with each other in the detector chamber when, for example, 90% argon/10% methane gas is used as the reagent gas. First, the argon atoms react with the beta particles emitted by the $^{63}$Ni detector cell to produce a high energy argon atom. At high pressures, where a large concentration of methane is present, the methane molecules react with the high energy argon atoms and emit electrons. The high energy electrons are slowed down by collisions with methane molecule and argon. In electron capture processes, the organic molecules can then capture the electrons produced. At lower pressures, little methane is present so the organic molecules are free to react with the high energy argon atoms to emit electrons. This is what is believed to happen in the electron emission process. When high concentrations of the organic compound such as methane are present in the reagent gas, the organic molecules can more efficiently slow down the electrons being produced so that the organic molecules eluted from the GC can undergo electron capture at lower pressures:

$$Ar + \rightarrow Ar^* \tag{a}$$

$$Ar^* + CH_4 \rightarrow Ar + CH_4^+ + e^- \tag{b}$$

$$M + e^- \rightarrow M^- \tag{c}$$

$$Ar^* + M \rightarrow Ar + M^+ + e^- \tag{d}$$

(a) Argon reacts with beta particle to give high energy atom;
(b) High energy argon atom reacts with methane to given electron;
(c) Electron capture process: organic molecule becomes ionized by electron produced in reaction (b);
(d) Electron emission process: organic molecule reacts with high energy argon atom to produce an electron.

The above description has been limited to Ar/CH$_4$ gas mixtures. In addition to a mixture of Ar/CH$_4$ gas being used as the reagent gas, oxygen, nitrogen, helium and hydrogen are suitable, as are the nobel gases besides argon, for example, neon, krypton and xenon. Mixtures of these gases are also suitable. Organic compounds besides methane which are useful include generally any compound or mixture of compounds having a vapor pressure at room temperature of at least about 10 torr. This encompasses a wide range of organic compounds including substituted and unsubstituted straight chained, cyclic and aromatic compounds, wherein the substitutions can include halogen, nitrogen, oxygen or sulfur.

Oxygen may be added to a reagent gas by mixing 99% argon/1% oxygen gas with the Ar/CH$_4$ gas in various ratios. With the oxygen added, the response for several of the compounds is enhanced in the electron capture mode of the detector. This enhanced response is thought to be due to reactions of oxygen with the eluted organics to form compounds with higher electron affinities.

The effect of oxygen provides an additional means of obtaining selectivity. For example, if the electron capture cell is run at atmospheric pressure with the cell open to atmosphere, a "typical" ECD response is obtained. However, if the cell is run at atmospheric pressure (760 torr) but is closed to atmosphere (e.g. gas exits into vacuum pumps instead of atmosphere), a different response is observed. This difference is believed due to diffusion of oxygen back into the cell when it is run exposed to atmosphere. This effect can lead to irreproducible results in conventional ECD detectors due to the dependence of back diffusion on carrier gas flow rates and cell design.

With nitrogen used as a reagent or carrier gas, the zero-crossing pressures have a much larger dependence on concentration of the compound compared with Ar/CH$_4$ due to less efficient electron thermalization. When helium is used as the reagent or carrier gas, the zero-crossing pressures are spread out over a wider range of pressures (100–400 torr) than they are with a Ar/CH$_4$ gas mixture, and the sensitivity in the capture mode is decreased 40 times without a quenching molecule present.

Although electron affinity values have heretofore been determined by atmospheric pressure electron capture cells, the use of the reduced pressures of the invention is considered superior since there is a lessened risk of interfering chemical reactions such as back diffusion of oxygen which may affect measurement accuracy. It is noted, for example, that many of the reported values of electron affinity obtained under atmospheric conditions do not agree with the theoretical values.

With regard to the particular design of the electron capture detector cell, either a "pulsed mode" or a "direct current mode" (DC mode) detector may be used. DC mode detectors are suitable in particular for the study of dynamic equilibrium but are less sensitive or versatile than pulsed-mode detectors. The advantages of pulsed-mode detectors are well known, and include a higher sensitivity and dynamic range compared to DC detectors. In pulsed-mode detectors, rather than supplying a DC current across the electrodes, a square wave pulse is used having a duration of from about 0.5 to about 14 sec at intervals of from about 0.05 to about 2 msec. Not only sensitivity, but the additional "time" variable available afforded by the pulsed mode adds further dimensions to the usefulness of the detector at low pressure by allowing controlled chemical reactions to occur during the time interval between detection pulses. Full advantage may thus be taken of selective ion-molecule reaction processes.

The following examples illustrate the invention.

EXAMPLES

Description of Apparatus

The system used in the examples consisted of a Varian model 1200 DC-mode (non-pulsed) electron capture cell which was enclosed in a stainless steel chamber connected to a high vacuum manifold. Pressure within the chamber was controlled by a Nupro precision needle valve mounted between the vacuum manifold and the detector cell. A high-capacity throttle valve connected in parallel with the needle valve enabled maximum pumping speed/high vacuum experiments to be performed. Chamber pressures were monitored by means of a Hastings thermocouple gauge (1–1000 millitorr) and a Schaevitz P702-0025 pressure sensor calibrated from 0–760 torr.

A gas mixing manifold was connected to the inlet of the detector cell for the purpose of mixing reagent gases with the GC eluent. A Nupro fine metering valve was used to control flow of the reagent gas into the system. Flow rates were monitored by means of 0–100 ml/min variable area flowmeters.

The gas chromatograph utilized was a Perkin-Elmer Model 3920 equipped with an on-column injector and a 25 meter $\times$ 0.25 mm (SE-52 stationary phase) fused silica capillary column. A $\frac{1}{8}'' \times 14''$ heated stainless steel transfer line connected between the GC oven and the detector cell routed the capillary column to the inlet of the detector cell. Capillary direct interfacing was employed to minimize dead volume effects of the long transfer line. The vacuum seal between the column and transfer line was made via a $\frac{1}{8}'' \times 1/16''$ SWAGELOK® coupling equipped with a graphite/vespel ferrule. The transfer line and vacuum chamber were heated with heat tape and thermally insulated with fiberglass tape. Temperature regulation was provided by a thermocouple feedback, variable temperature control unit. Both the chamber and transfer line were maintained at 280°–300° C.

The electrometer was a Varian model 1200 ECD/FID unit that had been modified for stand-alone operation. Chromatograms were recorded on a Linear Instruments model 155/mm strip chart recorder.

The mounting base for the detector cell was a stainless steel $2\frac{3}{4}''$ conflat flange. A $1\frac{1}{2}'' \times 5''$ stainless steel conflat extension tube served as the vacuum chamber. Electrical connections to the cell were made with $\frac{1}{4}''$ CAJON® Ultra-torr "O-ring" fittings. Water cooling coils were wrapped around the feedthrough connectors to minimize heat damage to the O-rings since the chamber temperature was maintained at about 300° C.

The electrical feedthroughs were specifically designed to enable rapid disassembly and reassembly of the detector system. Connections at the cell electrodes were made by spring clips. Standard BNC jacks on the high pressure side provided convenient connection to the electrometer. High temperature epoxy was used to seal the electrode, and a ceramic insert provided electrical insulation.

To improve pumping speed through the detector cell, the length of the outlet tube was reduced to 4 mm. Back diffusion of gas into the cell was generally not a problem due to the high pumping capacity of the vacuum system.

Operating Parameters

In order to optimize the response for any one mode of operation, the effects of three different parameters were investigated: (1) cell pressure, (2) flow rate of reagent gas through the cell, and (3) reagent gas composition. It is also quite probable that other parameters, including the potential applied to the cell electrodes and the operating temperature of the cell, will influence response. The examples, unless otherwise stated, were performed at 300° C. with an applied potential of −90 volts. Unless otherwise stated, the reagent gas and carrier gas used was argon with 10% methane (P-10 mixture). A molecular sieve/calcium chloride drying tube was used to remove moisture from the gas.

Although a reagent gas flow rate of 30 ml/min was best for conventional electron capture at atmospheric pressure, it was found that increasing the flow to 45-55 ml/min improved sensitivity at lower pressures. Also, due to reduced sensitivities in the argon ionization and mixed modes of operation, it was necessary to utilize an electrometer capable of responding to $10^{-11}$ amps.

EXAMPLE 1

Figure 3:
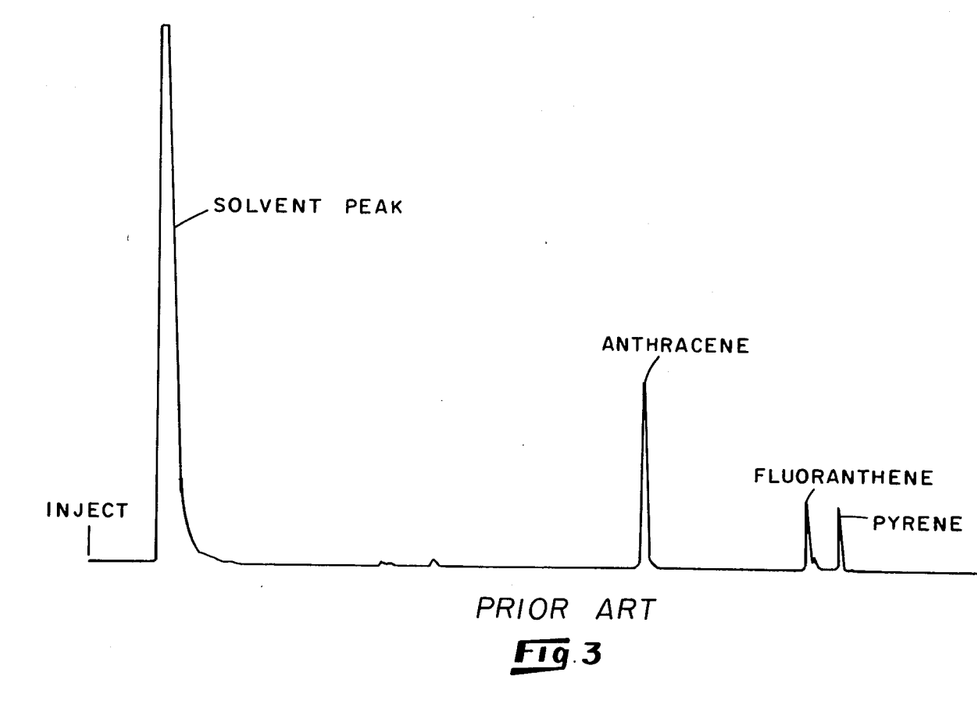
FIG. 3 is a conventional (atmospheric pressure) electron capture chromatogram of a 250 ppm mixture of phenanthrene, anthracene, fluorene and pyrene.
Figure 4:
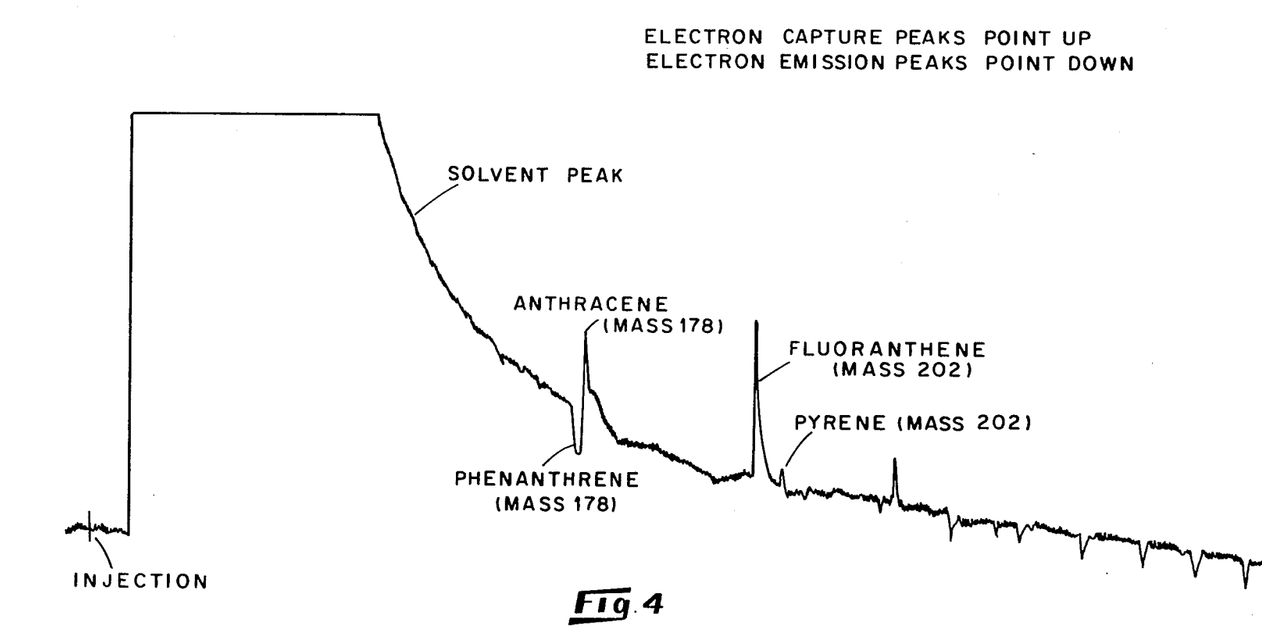
FIG. 4 is a reduced pressure ($\frac{1}{4}$ atmosphere) electron capture chromatogram of a 250 ppm mixture of phenanthrene, anthracene, fluoranthene, and pyrene.
Figure 5:
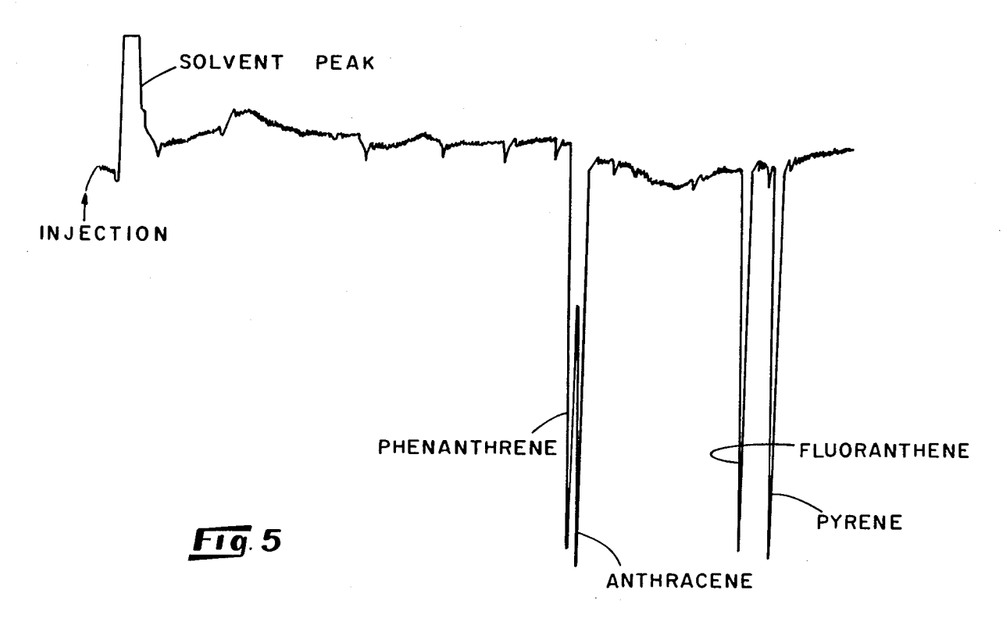
FIG. 5 is a low pressure (1/25 atmosphere) electron emission chromatogram of a 250 ppm mixture of phenanthrene, anthracene, fluoranthene, and pyrene.

A mixture of 2 sets of structural polycyclic aromatic isomers, anthracene and phenanthrene (mass 178), and fluoranthene and pyrene (mass 202) was run under (1) conventional electron capture conditions, (2) low pressure electron capture conditions, and (3) low pressure electron emission conditions. All compounds were present in the mixture at a concentration of 250 parts per million. The results are shown in FIGS. 3-5.

(1) Conventional conditions: When the electron capture cell was operated at atmospheric pressure, anthracene, fluoranthene, and pyrene appeared in the chromatogram shown in FIG. 3. Phenanthrene has a low electron affinity (0.03 eV) and therefore did not show up.

(2) Low pressure electron capture: At an operative pressure of approximately ¼ atmosphere, only anthracene and fluoranthene were observed to capture electrons (FIG. 4). Pyrene has a lower electron affinity and did not show up significantly, thus discrimination was achieved between the pyrene and fluoranthene isomers. In this chromatogram, phenanthrene was observed, but the peak was negative with respect to that of anthracene (due to electron emission). Again, isomeric discrimination was achieved.

(3) Low pressure electron emission mode: At a detector pressure of 30 torr (1/25 of atmosphere), the chromatogram shown in FIG. 5 was generated. This chromatogram displayed four peaks (one for each compound) of nearly equal intensity. These peaks were due to emission (as opposed to capture) of electrons (argon ionization) from the compounds. This result demonstrated that, under these conditions, all compounds could be observed if desired. This is important since at atmospheric pressures, only compounds with high electron affinities will show up in a chromatogram. In the electron emission mode, the detector response is similar to that of an argon ionization detector and is more uniform in response than a flame ionization detector.

This example illustrates that simply by varying the pressure of the reagent gases in an electron capture cell, essentially three different modes of operation can be achieved. Use of these modes demonstrates that each of the isomers in the test solution can be positively identified without the need for complex or expensive equipment such as a mass spectrometer or additional types of chromatographic detectors. The flexibility of this system is such that it could be the most useful GC detector currently available. Other unique advantages include:

1. Enhanced isomeric discrimination between compounds using only a gas chromatograph which does not require extensive separations or expensive equipment.

2. Variable pressure features allow the detector to be utilized in any of three modes: (1) conventional (atmospheric ECD), (2) low pressure electron capture (selective mode), and (3) low pressure electron emission (universal mode), 3. Emission mode gives "universal" response allowing all compounds to be observed in a mixture, i.e., either argon ionization for high sensitivity or cross-section ionization for high concentrations.

4. Selectivity in low pressure electron capture mode can be tailored by varying the pressure and composition of the reagent gas in the detector cell.

5. This single detector can be used in place of four different types of detectors, reducing the cost and complexity of the equipment.

Figure 6:
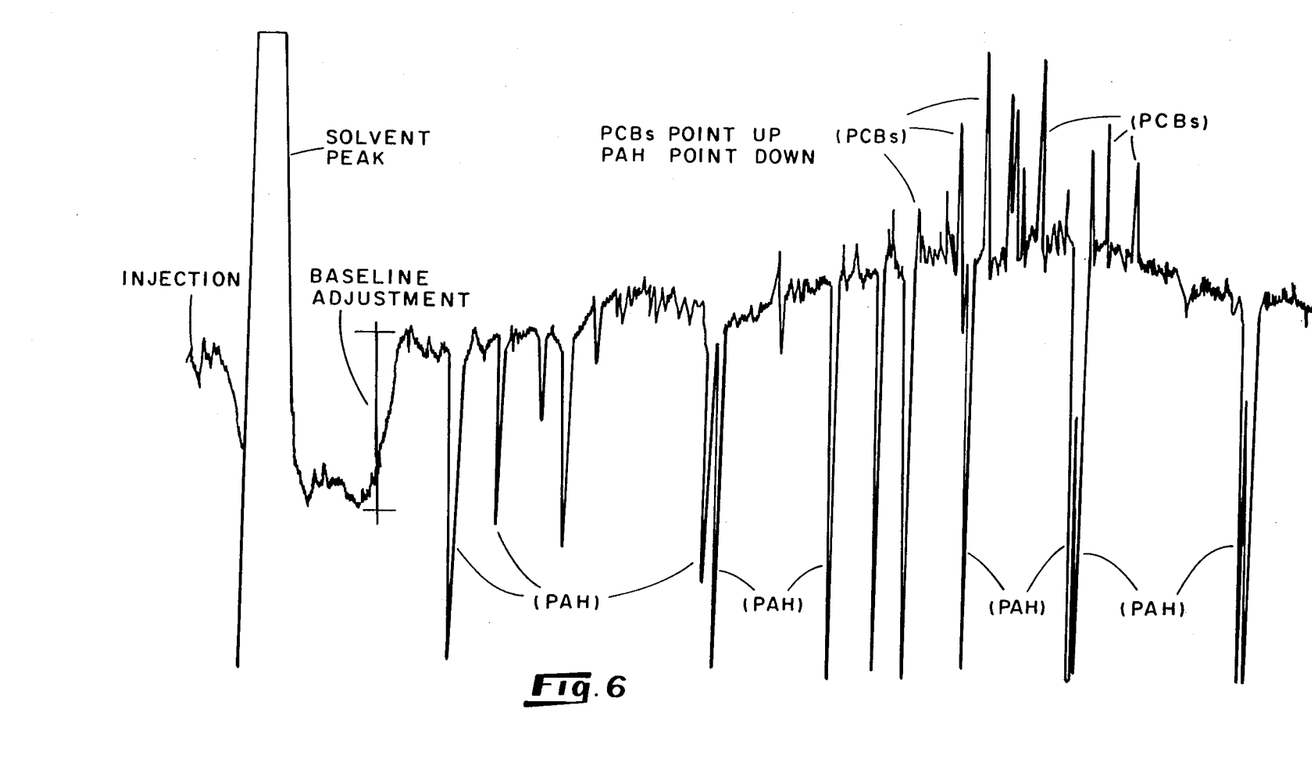
FIG. 6 is a reduced pressure (1/10 atmosphere) mixed electron capture/electron emission chromatogram of a 25 ppm mixture of polycyclic aromatic hydrocarbons (PAH) and polychlorinated biphenyls (PCB's).

In an alternative version, the detector can utilize a resistively heated filament (thermal ionization source) or another beta emitter, such as $^3$H, to replace the $^{63}$Ni ion source. This could be useful for more closely approximating the conditions found in a mass spectrometer ion source. Potential uses include isomeric discrimination in complex mixtures as well as compound "class" selectivity in the analysis of pollutants. An example of class selectivity is shown in FIG. 6 in which polychlorinated biphenyls (PCB's) can be distinguished from polycyclic aromatic compounds (PAH). Another potential use of this detector system would be as a detector for liquid chromatography or for supercritical fluid chromatography, or as an interface between a gas, liquid, or supercritical fluid chromatograph and a mass spectrometer.

PROCEDURES FOR EXAMPLES 2-7

For Examples 2 through 7, the variable pressure detector was used with a gas chromatograph to separate polycyclic aromatic hydrocarbons. Several pairs of isomeric PAH were able to be differentiated using this detector. Also, the responses of the detector to the compounds were compared to their electron affinity values.

Various combinations of PAH were used in the Examples and separated with the above-described Perkin-Elmer gas chromatograph. A solution was prepared containing 79 ppm of each compound in methylene chloride. First, the compounds were detected with the detector cell chamber at atmospheric pressure where conventional electron capture chromatography takes place. A 90% argon/10% methane gas mixture was used as the carrier and reagent gas at a flow rate of 30 ml/minute and a column pressure of 30 lbs/in². A 0.5 µl sample of solution was injected for each chromatogram at 300° C. The temperature in the column was held initially at 120° C. for 4 minutes and then raised at a rate of 8° C./minute until a final temperature of 300° C. was reached and held for 8 minutes.

EXAMPLE 2

Figure 7:
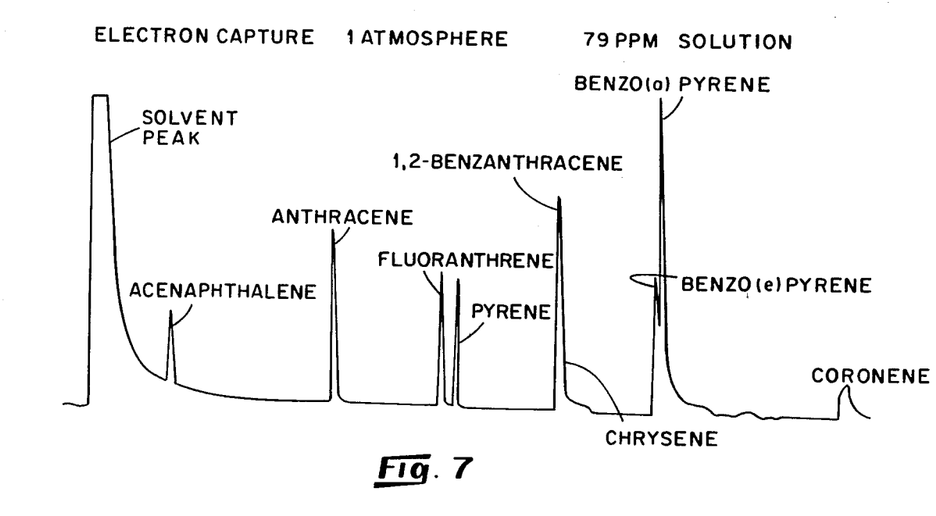
FIG. 7 is a conventional (atmospheric pressure) electron capture chromatogram of a 79 ppm mixture of 13 PAH compounds.

At atmospheric pressure, conventional electron responses were obtained (FIG. 7). Nine of the compounds, all of which had relatively high electron affinity values, were detected at 79 ppm and atmospheric pressure. Of these nine, four pairs of isomers were in the group of compounds, and these pairs either co-eluted or eluted very close together. The four compounds which were not detected were fluorene, phenanthrene, 2-phenylnaphthalene, and 2,3-benzofluorene. These four compounds have very low electron affinities (below 0.05 eV).

Very reproducible results were obtained at atmospheric pressure and relative responses were calculated for each of the compounds. Also, a concentration study was done at atmospheric pressure to determine if the responses of the detector at atmospheric pressure were linearly correlated with concentration. Five solutions, each containing five compounds ranging from 25 to 200 ppm each, were used. Peak heights were graphed against concentrations for each of the five compounds and linear correlations were obtained.

EXAMPLE 3

Twelve of the thirteen original PAH of Example 2 were analyzed at lower pressures. Coronene came out of the column at 300° C. and did not give sharp peaks. Therefore, it was no longer used.

At 1 torr, all of the PAH were in the electron emission mode, but the solvent was in the capture mode. The pressure was increased by approximately 100 torr intervals from 1 to 760 torr and by 10 torr intervals from 100 to 230 torr. As the pressure was increased, the compounds which changed from the electron emission mode to the electron capture mode at the lowest pressures had the highest electron affinity values. Therefore, the pressure study was used to find the pressures at which each of the compounds changed from the emission mode to the capture mode so that the zero-crossing pressures could then be compared to the electron affinity values of the compounds.

Figure 8:
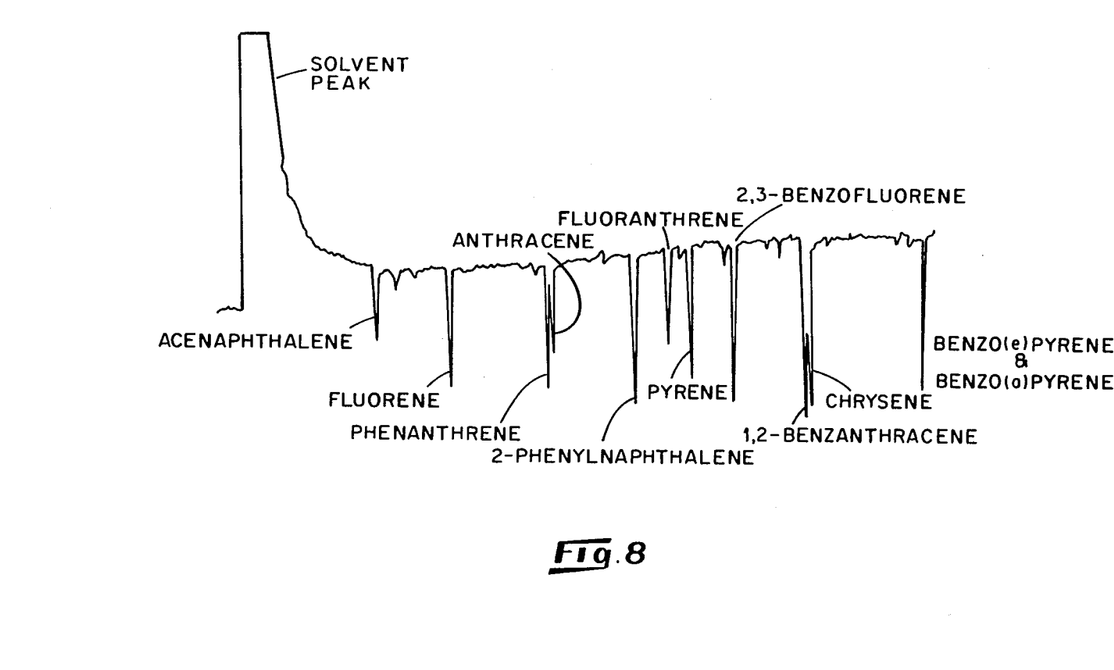
FIG. 8 is an electron emission chromatogram for 12 PAH at a pressure of 123 torr.
Figure 9:
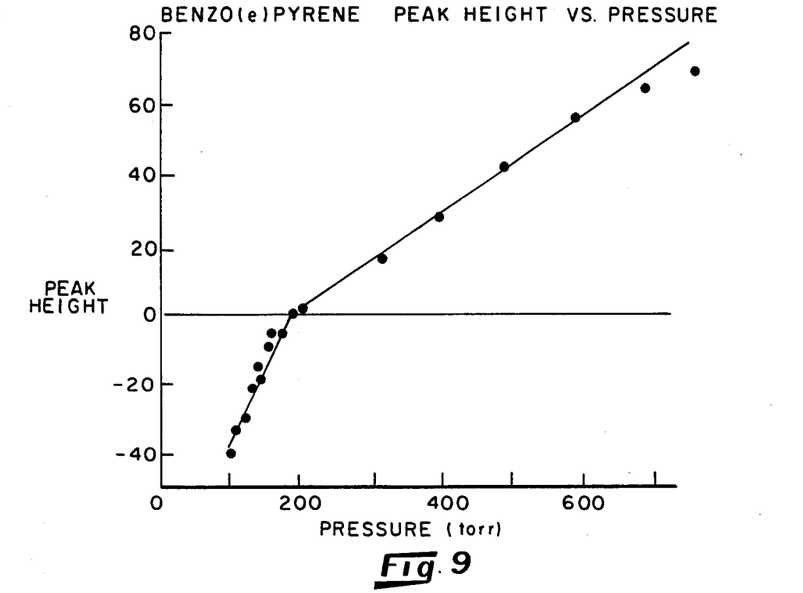
FIG. 9 is a graph of peak height versus pressure for benzo(e)pyrene.

The zero-crossing pressures for the PAH group ranged from 130 to 230 torr using a 90% Ar/10% $CH_4$ gas mixture. Maximum electron emission responses for all of the compounds were obtained between 100 and 125 torr (FIG. 8). At very low pressures (e.g. 1 torr), one fourth to one half of the response shown in FIG. 8 was obtained, and the relative responses were approximately equal. In FIG. 8, the relative responses at 123 torr vary because some compounds are going toward the capture mode. The zero-crossing pressures were obtained through graphs of peak height versus pressure for each of the compounds. The graph of benzo(e)pyrene is shown in FIG. 9. The zero-crossing pressure for a given compound was taken as the pressure at which the peak height approached zero or at which the direction of the peak changed. The pressures found had a +5 torr accuracy.

The zero-crossing pressures for each of the compounds were plotted against their electron affinity values (FIG. 10). The graph obtained shows a linear correlation between the two sets of values. The PAH with high electron affinities have lower zero-crossing pressures than the PAH with low electron affinities. Many different electron affinity values for the PAH compounds have been calculated but have not agreed well with any experimental methods. Therefore, the linear correlation between the zero-crossing pressures and the electron affinity values of the PAH in the study could lead to a method of determining the electron affinities of PAH compounds from their zero-crossing pressures.

The analysis was repeated and zero-crossing pressures for the PAH determined and graphed again against electron affinity values. The second graph agreed well with the first graph.

EXAMPLE 4

To differentiate between a pair of isomeric compounds, a pressure intermediate of the zero-crossing pressures of the two isomers is chosen. When the isomeric pair is detected with the detector cell chamber at this pressure, the isomer with the highest zero-crossing pressure will undergo electron emission while the other isomer will undergo electron capture. Therefore, their peaks will point in opposite directions, and the isomers will be differentiated easily.

Figure 11:
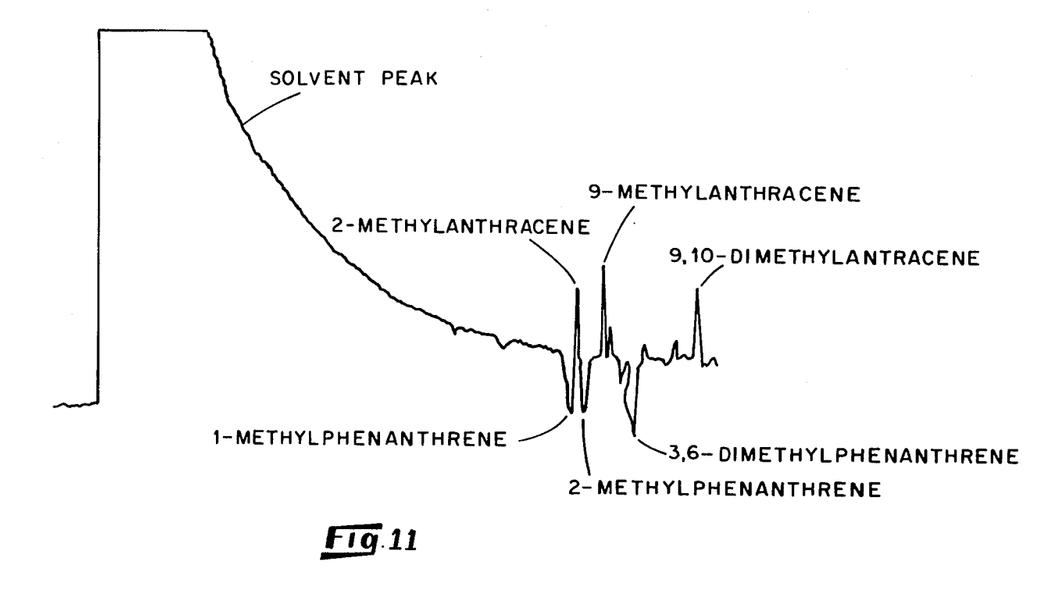
FIG. 11 is a chromatogram showing isomeric differentiation of three methylated anthracenes and three methylated phenanthrenes at a pressure of 175 torr.

A solution of three methylated anthracenes and three methylated phenanthrenes was detected at a pressure of 175 torr, intermediate of the zero-crossing pressures of phenanthrene and anthracene (FIG. 11). The anthracenes were all in the capture mode with thier peaks pointing down. Just by knowing the zero-crossing pressures for a pair of isomers, isomeric differentiation can be easily obtained.

EXAMPLE 5

Figure 12:
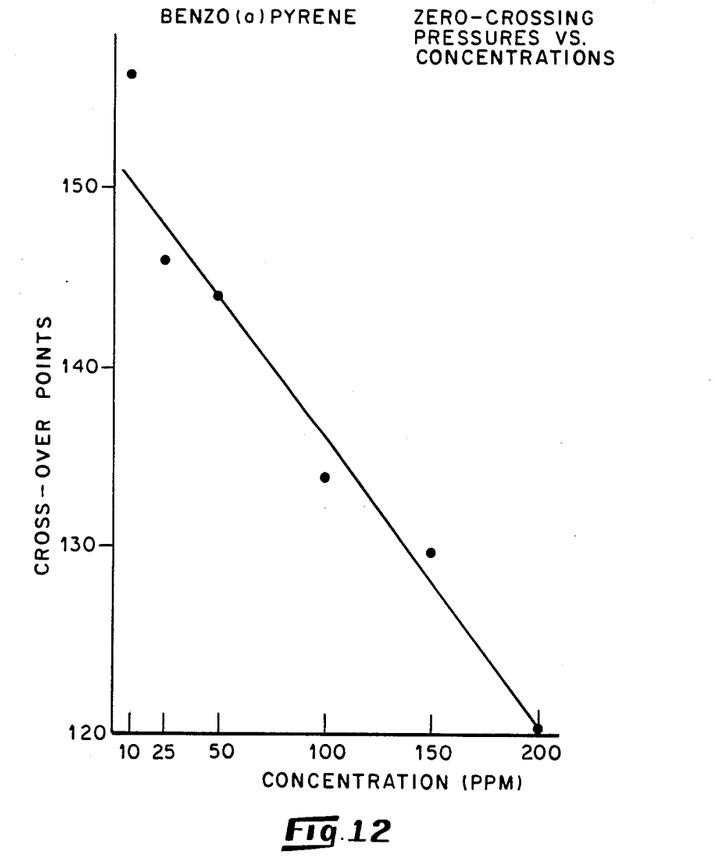
FIG. 12 is a graph of zero-crossing pressure versus con-centration for benzo(a)pyrene.

A concentration study was conducted to determine the effect concentration has on zero-crossing pressures. A set of solutions containing five PAH each in equal concentrations ranging from 5 to 200 ppm was prepared. All solutions were separated at several different pressures. For higher concentrations, the zero-crossing pressures were observed to be lower than at lower concentrations. Graphs were made of zero-crossing pressures versus concentrations for four of the five compounds, and linear correlations between the sets of values were obtained. Benzo(a)pyrene (FIG. 12) had the largest concentration dependence of 30 torr for a 200 ppm concentration range, while the other three compounds had about a 10 torr variance for a 200 ppm concentration range.

EXAMPLE 6

Figure 13:
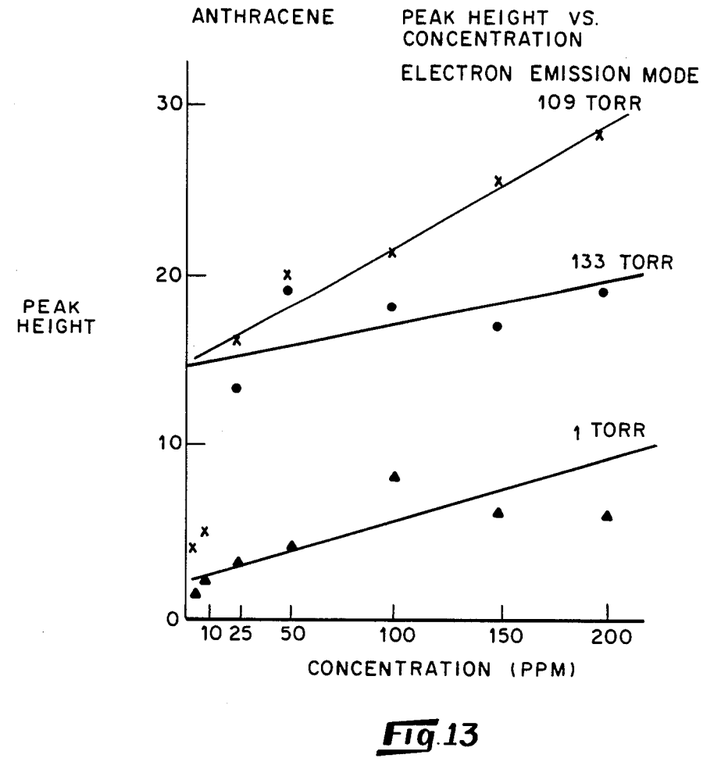
FIG. 13 is a graph of peak height versus concentration in the electron emission mode for anthracene at three different pressures.

Concentration studies were performed at low pressures (where all of the PAH are in the emission mode) to determine the linearity of the response to concentration in the electron emission mode of the detector. Graphs of peak height versus concentration were made for the compounds, and a linear correlation between peak heights and concentrations was found for the emission mode as was found for the capture mode. The responses in the electron emission mode were measured at three different pressures, 1 torr, 109 torr and 133 torr. Peak heights at all three pressures were plotted against concentration for the five compounds. Anthracene is shown in FIG. 13. At 109 torr, where electron emission responses were best, the slopes of the plots were fairly large. At 133 torr, where the pressure approached the cross-over points of the compounds, the slope was smaller, and more deviation from the line was found. Also, at 1 torr, where responses were very small, peak heights did not vary much with concentration, so that the slope of the plots were small.

EXAMPLE 7

A mixture of benzo(a)pyrene (EA=0.64 eV) and benzo(e)pyrene (EA=0.35 eV) is run at a pressure of 160 torr. The benzo(e)pyrene elutes a few seconds prior to benzo(a)pyrene and produces a negative response due to its significantly lower electron affinity. The benzo(a)pyrene undergoes electron capture and produces a positive response. This example illustrates the usefulness of the invention in identifying constituents for which standards are not readily available or for constituents that are not well resolved chromatographically. Prior art detection of benzo(a)pyrene, which is a potent carcinogen, is often hampered by the co-elution of benzo(e)pyrene, which is relatively benign.

The foregoing description of preferred embodiments has been set forth merely to illustrate the invention and is not intended to be limiting. Since modifications of the described embodiments incorporating the spirit and substance of the invention may occur to persons skilled in the art, the scope of the invention should be limited solely with respect to the appended claims and equivalents.

We claim:

1. A method for measuring a zero-crossing pressure for an organic compound, comprising the steps of:
   (a) injecting a sample of a gaseous mixture containing at least one organic compound into an electron capture detector cell;
   (b) maintaining a discrete pressure in said cell, said pressure being atmospheric pressure or below;
   (c) detecting the variation in electrical current in said cell due to one of capture and emission of electrons by said organic compound;
   (d) repeating the sequence of steps (a) through (c), wherein the pressure in said cell is adjusted in each succeeding sequence to be higher or lower than the preceding sequence depending on which of emission or capture respectively is detected in step (c), said sequence being repeated until the detected variation of said electrical current is minimized and the zero-crossing pressure thereby obtained.

2. A method for measuring a zero-crossing pressure for an organic compound, comprising the steps of:
   (a) maintaining a constant flow of a gaseous mixture containing at least one organic compound through an electron capture detector cell;
   (b) varying the pressure in said cell by pulsing a reagent gas into said cell;
   (c) recording an electron current generated during step (b);
   (d) correlating said recorded electron current as a function of said varying pressure;
   (e) obtaining a zero-crossing pressure as the pressure corresponding to a minimum value of said generated electron current.

3. A method as claimed in claim 2 including the step of subtracting from said recorded electron current a background current due to said reagent.

4. A method for detection and differentiation of organic compounds by electron affinity, comprising:
   (a) injecting a gaseous mixture containing at least two organic compounds into an apparatus for detection and differentiation of organic compounds by electron affinity comprising:
      (i) an electron capture detector cell;
      (ii) means for injecting gaseous compounds in said cell;
      (iii) means for detection and measurement of electric current variation in said cell, said electric current variation being a function of the composition of said gaseous compounds in said cell; and
      (iv) means for providing a subatmospheric pressure in said cell;
   (b) maintaining the pressure in said electron capture detector cell at or below a zero-crossing pressure of at least one of said at least two organic compounds, and at or above a zero-crossing pressure of at least another of said at least two organic compounds;
   (c) detecting the variation in electrical current in said cell due to one of capture and emission of electrons by said organic compound; and
   (d) differentiating said organic compounds based on the electrical current variations due to the capture or emission of electrons by said organic compounds.

5. A method as claimed in claim 3, wherein the pressure in said cell is maintained at or below a zero-crossing pressure of each of said at least two organic compounds.

6. A method for detection and differentiation of organic compounds by electron affinity, comprising:
   (a) injecting a gaseous mixture containing a plurality of organic compounds into an apparatus for detection and differentiation of organic compounds comprising:
      (i) an electron capture detector cell which is closed to the atmosphere;
      (ii) means for injecting gaseous compounds into said cell;
      (iii) means for detection and measurement of electric current variation in said cell, said electric current variation being a function of the composition of said gaseous compounds in said cell; and
      (iv) means for providing a subatmospheric pressure in said cell;
   (b) maintaining the pressure in said electron capture detector cell below atmospheric pressure;
   (c) detecting the variation in electrical current in said cell due to one of capture and emission of electrons by each of said organic compounds; and
   (d) obtaining a zero-crossing pressure for each of said organic compounds.

* * * * *